(12) United States Patent
Richards

(10) Patent No.: US 6,374,668 B2
(45) Date of Patent: Apr. 23, 2002

(54) GAS ANALYZER

(76) Inventor: Dean John Richards, 4002 Norwood, Midland, TX (US) 79707

( * ) Notice: Subject to any disclaimer, the term of this patent is extended or adjusted under 35 U.S.C. 154(b) by 0 days.

(21) Appl. No.: 09/801,554

(22) Filed: Mar. 8, 2001

Related U.S. Application Data

(60) Provisional application No. 60/189,102, filed on Mar. 14, 2000.

(51) Int. Cl.[7] .................. E21B 47/00; C09K 7/00; G01N 33/24
(52) U.S. Cl. .................. 73/152.04; 175/42; 73/19.09
(58) Field of Search .................. 73/152.04, 152.02, 73/19.09; 166/250.01; 175/42, 48; 367/69

(56) References Cited

U.S. PATENT DOCUMENTS

| | | | | |
|---|---|---|---|---|
| 2,341,169 A | * | 2/1944 | Wilson et al. | 73/152.04 |
| 2,489,180 A | * | 11/1949 | Hayward | 73/152.04 |
| 3,050,449 A | * | 8/1962 | Moore | 202/152 |
| 4,635,735 A | * | 1/1987 | Crownover | 175/48 |
| 4,887,464 A | * | 12/1989 | Tannenbaum et al. | 73/152.04 |
| 5,090,256 A | * | 2/1992 | Issenmann | 73/863.23 |
| 5,237,539 A | * | 8/1993 | Selman | 367/69 |
| 5,277,263 A | * | 1/1994 | Amen | 175/42 |
| 5,447,052 A | * | 9/1995 | Delaune et al. | 73/19.09 |
| 5,469,917 A | * | 11/1995 | Wolcott | 166/250.01 |
| 5,648,603 A | * | 7/1997 | Hanson | 73/152.02 |
| 6,276,190 B1 | * | 8/2001 | Zamfes | 73/19.01 |

* cited by examiner

Primary Examiner—Hezron Williams
Assistant Examiner—Jay L Politzer
(74) Attorney, Agent, or Firm—Wendell Coffee

(57) ABSTRACT

A gas analyzer for an oil drilling rig normally flows gas captured from a mud pit source through parallel paths from the gas source to a total gas analyzer. One of the paths is a loop path. Periodically the loop path is switched from the source to the total gas analyzer and connected to a path from an air supply to a chromatograph. After a short time during which the gas from the loop path is transferred to the chromatograph then the loop path is switched back to the original parallel path. This arrangement permits a small instrument to perform both the functions of total gas analyzer and chromatograph.

9 Claims, 2 Drawing Sheets

292 SECOND MODE

8 SECOND MODE

GAS ANALYZER

CROSS REFERENCE TO PROVISIONAL PATENT APPLICATION

The applicant claims the benefit of his U.S. Provisional Application No. 60/189,102 filed Mar. 14, 2000.

BACKGROUND OF THE INVENTION (1) Field of the Invention

This invention relates to analyzing gas from the mud produced by drilling an oil well.

Oil well drilling mud is forced in the drill pipe into the bore hole and circulated from the bit back to the surface of ground. When the drill bit is in a zone wherein petroleum is present, a certain amount of the light gases in the methane series make their way into the mud stream. When the mud stream is circulated to the surface these gases are analyzed. The technique of capturing the gases from the mud is well known in the art. Drilling superintendent have ordinary skill in this, the gas analyzing art.

(2) Description of the Related Art

Before this invention, the total gas from the mud pit was analyzed by a sperate instrument named Total Gas Analyzer (TGA) to determine the total amount of gases produced. Also the amount of each individual gas was determined by a second instrument named a Chromatograph (CG). That is, the quantity of methane, ethane, propane, isabutane, butane and pentane were each measured by the chromatograph as to the amount each was present.

SUMMARY OF THE INVENTION (1) Progressive Contribution to the Art

This invention combines the two instruments into one small unit. With a single unit the total gas produced and the amount of each gas is determined.

The only lines to the gas analyzer of this invention are a single gas line from the mud pit and a single electric power line.

The results of analysis are automatically continually available. The results may be recorded every 5 minuets.

(2) Objects of this Invention

An object of this invention is to continually measure the volume and increase the accuracy of the measurements of the gas.

Also an object of this invention is to quickly and accurately analyze the gas by a compact instrument which does not require excessive space upon the drilling platform.

Other objects are to achieve the above with an instrument that is easy to operate by workers having little skill in electronics, physics, or chemistry.

Further objects are to achieve the above with devices that are sturdy, compact, durable, lightweight, simple, safe, efficient, versatile, ecologically compatible, low maintance, energy conserving, and reliable, yet inexpensive and easy to manufacture, install, operate, and maintain.

Other objects are to achieve the above with a method that is rapid, versatile, ecologically compatible, energy conserving, efficient, and inexpensive, and does not require highly skilled people to install, operate, and maintain.

The specific nature of the invention, as well as other objects, uses, and advantages thereof, will clearly appear from the following description and from the accompanying drawings, the different views of which are not necessarily scale drawings.

CALOGUE OF ELEMENTS

Figure 1:
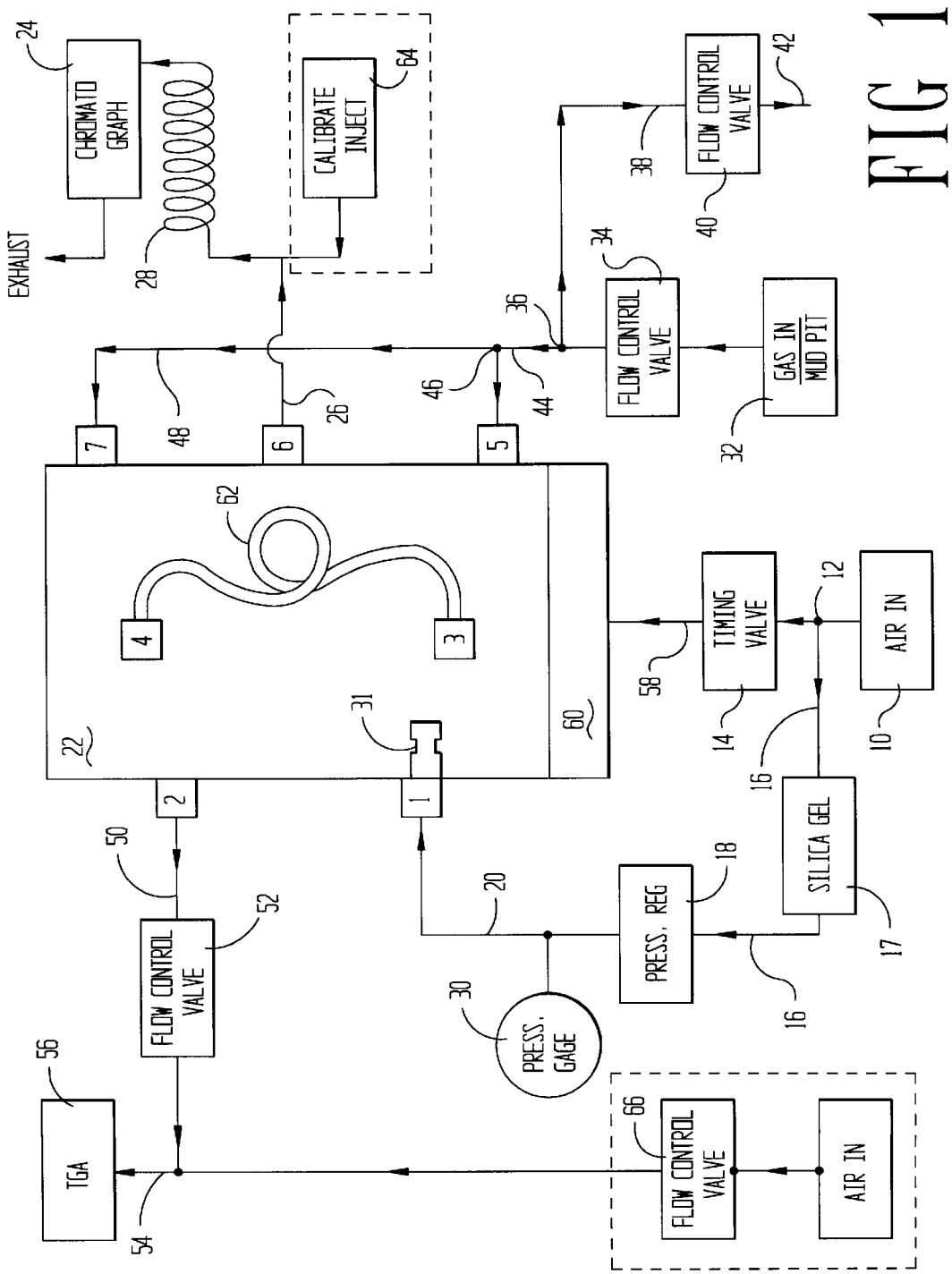
FIG. 1 is a schematic representation of the analyzer.

As an aid to correlating the terms of the claims to the exemplary drawing(s), the following catalog of elements and steps is provided:

1. Air In Port
2. TGA Port
3. Loop Port
4. Loop Port
5. Gas In Port
6. CG Port
7. Gas In Port
10 Air Intake
12 T-Joint
14 Timer Valve
16 Line
17 Silica Gel Scrubber
18 Pressure Regulator
20 Output Line
22 Sample Valve
24 Chromatograph CG
26 Line CG
28 Separator
30 Gauge
31 Orifice
32 Mud Pit
34 Flow Control Valve
36 T-Joint
38 Line
40 Flow Control Valve
42 Line
44 Line
46 T-Joint
48 Line
50 Line
52 Flow Control Valve
54 Line
56 Total Gas Analyzer (TGA)
58 Line
60 Activator
62 Loop
64 Calibration Inject
66 Dilution Flow control Valve

DESCRIPTION OF THE PREFERRED EMBODIMENTS(S)

The drawing shows atmospheric air is pumped by a pump (not shown), into the system at intake 10. The air flows through a T-joint 12 at a timer valve 14. The majority of the air passes on through line 16 with silica gel scrubber 17 to the pressure regulator 18. The air from the pump will be at about 9 psig in the line 16. The scrubber is well known to the art and prevents foreign material from fouling precision equipment. Pressure regulator 18 will reduce the pressure to precisely 8 psig into line 20 which extends to sample valve 22. Gage 30 displays the pressure in line 20.

As will be explained later, the sample valve 22 will feed a precise predetermined sample to Total Gas Analyzer TGA 56 by line 50 from the sample valve 22.

Describing the sample valve 22 in detail: the sample valve will have seven ports identified as AIR IN PORT 1, TGA PORT 2, LOOP PORT 3, LOOP PORT 4, GAS IN PORT 5, CG PORT 6 and GAS IN PORT 7. The line 20 is connected to AIR IN PORT 1.

In the normal position, which is the position of the sample valve for 4 min. and 52 seconds (292 seconds) of each 5 min, the AIR IN PORT 1 will be connected to CG PORT 6 through orifice 31. Stated otherwise, in the normal position of the sample valve 22, AIR IN PORT 1 will be connected to CG PORT 6 and the air will flow through line 26, through column 28, and through the chromatograph (CG)24. Therefore the majority of time there will be air flowing through the chromatograph 24.

The gas from the mud pit is captured as shown at pit 32. As stated before the process of capturing gas from the mud pit is well known in the art. The gas will be captured at a rate anywhere from 3 standard cubic feet an hour (scfh) to 10 scfh. Normally it will be adjusted to capture about 6 scfh. Flow control valve 34 will be set to have an output of 6 scfh. The output of the flow control valve 34 is split by T-joint 36 with the line 38 going to flow control valve 40 which will exhaust 3 scfh to exhaust through line 42. Line 44 from the T-joint 36 will therefore also carry 3 scfh.

The line 44 is connected to GAS IN PORT 5 at T-joint 46. The other exit of the T-joint 46 is connected to line 48 which is connected to GAS IN PORT 7.

Figure 2:
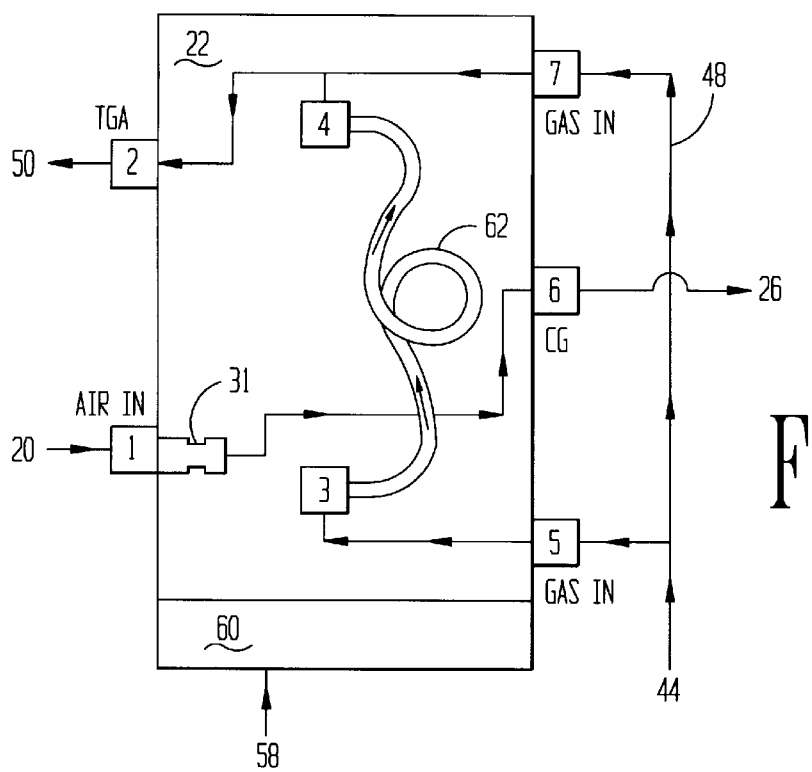
FIG. 2 is a schematic representation of the sample valve showing the flows and connections in the 292 second mode.

Referring to FIG. 2 in normal position (292 second mode) the GAS IN PORT 7 is connected to the TGA PORT 2 and the LOOP PORT 4. The LOOP PORT 3 is externally connected by loop 62 to LOOP PORT 4.

Also GAS IN PORT 5 is connected to LOOP PORT 3. Thus, gas from the mud pit 32 circulates through the loop 62 as well as directly into the total gas analyzer 54 during the 292 second mode. Stated otherwise, these are parallel paths for the gas to flow from line 44 into the total gas analyzer. One path is from GAS IN PORT 7 to TGA PORT 2. The other path, something called the loop path, is from GAS IN PORT 5 through loop 62 and into TGA PORT 2.

The sample valve body 22 has an internal orifice 31 in the form of a small diameter bore permanently connecting the AIR IN PORT 1. As stated above, the pressure in the line 20 is fixed by the pressure regulator 18 and monitored by the gage 30. By this arrangement the air flows from AIR IN PORT 1 to CG PORT 6 in the 292 second mode (normal position).

TGA PORT 2 is connected to line 50 which extends to flow control valve 52. The flow in line 50 will be 1 scfh. The flow control valve 52 will maintain the flow in line 54 at 1 scfh. This line 54 is connected to the total gas analyzer 56.

The timer valve 14 is controlled by a timer (not shown) so that every 5 min. it activates to open the timer valve so that line 58 is connected to the line 16 for eight (8) seconds. The line 58 will carry at least 8 psig and be connected to activator 60 of the sample valve 22. The activator will move a diaphragm which will shift a plunger in the sample valve which will change the connections of the ports.

Figure 3:
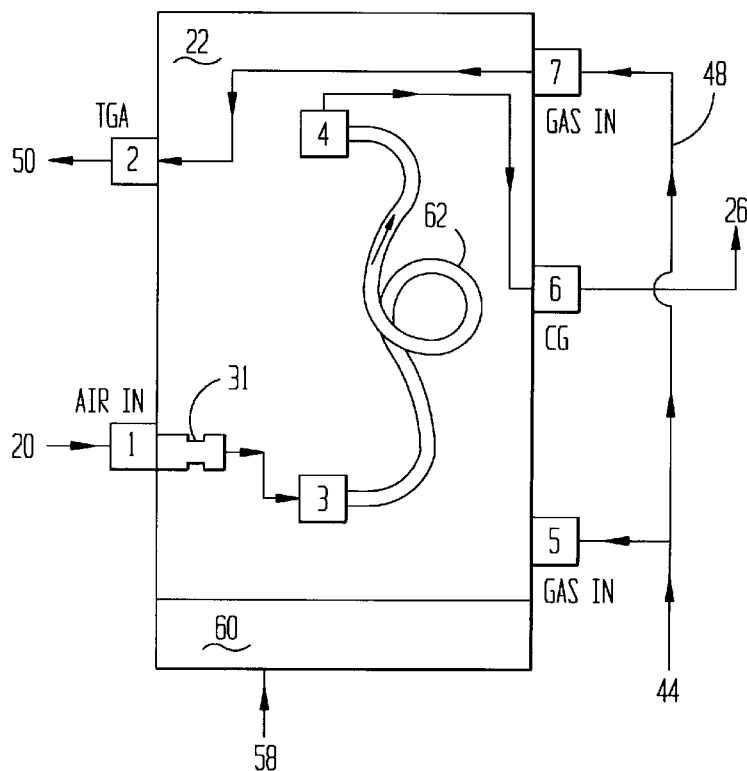
FIG. 3 is a schematic representation of the sample valve showing the flows and connections in the 8 second mode.

FIG. 3 shows the connections in the valve 22 during the 8 seconds mode (also called closed position).

The preferred form of the sample valve is a plunger running through a sleeve. O-rings on the plunger fit along the sleeve so that when the plunger is moved by the activator 60 that it will make the connections as described. However other means could be made to make these connections. The plunger type operation is preferred because of its compact size.

During this 8 sec. time (when the sample valve is in the closed condition) the LOOP PORT 4 is shifted from GAS IN PORT 7 to CG PORT 6.

The GAS IN PORT 5 is not connected within the valve 22. GAS IN PORT 7 is connected to TGA PORT 2. Therefore there will be a continual flow of gas through this path to the total gas analyzer 56.

Also the AIR IN PORT 1 is shifted from CG PORT 6 and connected to LOOP PORT 3 through the orifice 31.

CG PORT 6 will be connected to LOOP PORT 4. LOOP PORT 3 and LOOP PORT 4 are connected by loop 62.

During normal time (292 second mode) the loop 62 will be loaded with gas from GAS IN PORT 7 connected to LOOP PORT 4 as described above.

At the time when the valve is switched from normal to closed position (FIG. 3), the gas within this path, the loop 62, will be expelled through LOOP PORT 4 connected to the CG PORT 6. The air from AIR IN PORT 1 will flow through the orifice 31 into LOOP PORT 3. The air will push the accumulated gas in this path, the loop 62, out through the CG PORT 6 which will take the gas through the separator 28 and chromatograph 24. The chromatograph will show the amounts of each of the gases present.

At the end of the 8 second mode, the timer on valve 14 will close valve 22 and the 292 second mode will start.

Timer valves are well known. The preferred timer valve is the Mini Myte manufactured by Humphries Mfg. Co. Box 2008 Kalamazoo Mich. 49003. The timer (not shown) for the timer valve is preferred to be the timer made by Industrial Timer Inc. Centerbrook, Conn. 06409.

The equipment is designed to be operated electrically at 2 volts dc. A converter, not shown, produces 2 volt dc from 110 voltage ac source.

The separator column 28 is made of copper ¼ in. O.D. copper tubing 70 inches in length. It is coiled to conserve space. The column is packed with granulated diabutial phthilate, a product manufactured by Kodak Chemical of Rochester N.Y. It is provided as a liquid rubber.

The packing material is prepared by use of laboratory grade chromosorb P which has not been acid washed (known as non-acid wash). The chromosorb P is crushed and used at a size of 60–80 mesh. Next, a mixture of enough acetone to throughly mix with the diabutial phthilate, is prepared. Then enough of this mixture is poured over the crushed chromosorb P non-acid wash to completely coat the crushed chromosorb P. It is stirred until the acetone is evaporated. Thus small particles or granules are produced having a diabutial phthilate coating.

Good results are obtained with one (1) unit by weight diabutial phthilate mixed with four (4) units by weight of acetone. This mixture poured over two (2) units by weight of crushed chromosorb P.

The packing thus prepared is placed into the copper tubing forming the separation column 28.

As is well known, the chromatograph will measure the first gas to be released from the column 28 which will be the methane. After the methane is measured, the second gas to be released from the separator will be ethane, after it is measured the next will be propane and so forth to pentane.

The measurement of the amount of gases is the same in the total gas analyzer and the chromatograph. That is to say, the gases are measured by the heat units they produce as they are flowed over a heated special material. Traditionally the material was platinum. The preferred material is thermistor beads. The thermistor beads are a product of J. J. Enterprises in Baton Rough, La.

Many different features may be included which are not essential for normal use. For example calibration inject 64 provides for a known sample of the gases may be injected into the air stream of the line 26 during 292 second mode. They would be carried to the separator 28 and the results shown at the chromatograph 24. However this is standard on substantially all gas analyzers.

Also in the event that there was some possibility there would be sufficient amounts of gases to cause the total gas analyzer to go off the scale, (exceed its capacity) then it is possible to have an air dilution stream connected from an air flow to the flow control valve 52. An equal amount of air is pumped into flow control valve 66. Therefore diluting the sample going to the total gas analyzer to one half the otherwise calculated value.

It will be understood that the drawing is schematic drawing. On the apparatus the information produced by the total gas analyzer and the chromatograph, and other items will be displayed on a front panel for open inspection.

Although the equipment is described as obtaining a chromatograph reading each five minuets, some events of drilling may make a special immediate chromatograph reading desirable.

Although it is not shown the timing valve may be manually energized to take a reading. Also if the total gas analyzer indicates an extreme sudden increase of the gas produced, a special chromatograph reading may be produced responsive to the extreme sudden increase. Those with ordinary skill in the art could readily provide such a response.

The embodiment shown and described above is only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to point out the advantages and the progressive contribution to the art of analyzing the gas produced in oil well drilling and to enable one skilled in the art to make and use the invention. The limits of the invention and the bounds of the patent protection are measured by and defined in the following claims.

I claim as my invention:

1. The method of analyzing methane series of gas produced from a drilling rig, comprising:
   a) pumping a small gas specimen from a mud pit,
   b) flowing the small gas specimen to a sample valve,
   c) splitting the flow in the sample valve into a TGA stream and a CG stream,
   d) creating a closed time period and normal time period with the normal time period much longer than the closed time period,
   e) continually flowing, during normal time period and closed time period, the TGA stream to a total gas analyzer, and
   f) intermittently flowing during the closed time period the CG stream to a chromatograph.

2. The invention as defined in claim 1 further comprising:
   g) flowing the CG stream of gas through a loop and from the loop to the total gas analyzer during the normal time period, and
   h) flowing air into the loop and thus gas out of the loop into the chromatograph during the closed time period.

3. The invention as defined in claim 1 further comprising:
   g) periodically switching from normal time period to closed time period, about every five minuets.

4. The invention as defined in claim 1 further comprising:
   g) switching from normal time period to closed time period responsive to an extreme increase of total gas flow as indicated by the total gas analyzer.

5. The method of analyzing methane series of gas produced from a drilling rig, comprising:
   a) pumping a small gas specimen from a mud pit source,
   b) flowing the small gas specimen to a total gas analyzer by parallel paths, one of the paths being a loop path,
   c) at times switching the loop path from the parallel path, and
   d) connecting the loop path from an air supply to a chromatograph, and
   e) after a short time, switching the loop path back to the parallel path.

6. The invention as defined in claim 5 further comprising:
   f) periodically switching the loop path from the parallel paths to the air supply to chromatograph about every five minuets.

7. The invention as defined in claim 5 further comprising:
   f) switching the loop path from the parallel paths to the air supply to chromatograph responsive to an extreme increase of total gas flow as indicated by the total gas analyzer.

8. The invention as defined in claim 5 further comprising:
   f) at all times maintaining the rate of flow from the paths into the total gas analyzer to a fixed flow.

9. The invention as defined in claim 1 further comprising:
   g) at all times maintaining the rate of flow from the sample valve into the total gas analyzer to a fixed flow.

* * * * *